United States Patent
Pengpanich

(10) Patent No.: US 10,821,424 B2
(45) Date of Patent: Nov. 3, 2020

(54) PROCESS FOR PREPARING A CATALYST FOR ALKANE AROMATIZATION

(71) Applicant: PTT Global Chemical Public Company Limited, Bangkok (TH)

(72) Inventor: Sitthiphong Pengpanich, Bangkok (TH)

(73) Assignee: PTT Global Chemical Public Company Limited, Bangkok (TH)

( * ) Notice: Subject to any disclaimer, the term of this patent is extended or adjusted under 35 U.S.C. 154(b) by 0 days.

(21) Appl. No.: 15/906,785

(22) Filed: Feb. 27, 2018

(65) Prior Publication Data

US 2019/0262812 A1 Aug. 29, 2019

(51) Int. Cl.
*B01J 21/00* (2006.01)
*B01J 29/48* (2006.01)
*B01J 29/44* (2006.01)
*B01J 37/30* (2006.01)
*B01J 37/02* (2006.01)
*C07C 5/41* (2006.01)
*C07C 2/76* (2006.01)

(52) U.S. Cl.
CPC .............. *B01J 29/48* (2013.01); *B01J 29/44* (2013.01); *B01J 37/0215* (2013.01); *B01J 37/30* (2013.01); *C07C 2/76* (2013.01); *C07C 5/417* (2013.01); *B01J 2229/186* (2013.01); *B01J 2229/34* (2013.01); *C07C 2529/44* (2013.01); *C07C 2529/48* (2013.01)

(58) Field of Classification Search
CPC ........ B01J 29/48; B01J 37/0215; B01J 37/30; B01J 29/44; B01J 2229/34; B01J 2229/186; C07C 5/417; C07C 2529/48; C07C 2529/44

See application file for complete search history.

(56) References Cited

U.S. PATENT DOCUMENTS 5,574,199 A * 11/1996 Beck .................. B01J 29/40
585/400
2012/0215043 A1 * 8/2012 Gaffney ................ B01J 29/064
585/241

* cited by examiner

*Primary Examiner* — Haytham Soliman
(74) *Attorney, Agent, or Firm* — Troutman Pepper Hamilton Sanders LLP

(57) ABSTRACT

The present invention relates to a process for preparing a catalyst for alkane aromatization providing high % conversion, high yield, high selectivity of aromatics, and high selectivity of p-xylene in xylene, wherein said process comprises the following steps:
(a) contacting a zeolite with a solution of group IIIA metal salt;
(b) contacting the zeolite obtained from step (a) with the solution of metal salt selected from a group VIIB metal, a group VB metal, or a mixture thereof; and
(c) contacting the zeolite obtained from step (b) with alkoxysilane,
characterized in that the solution of salt in step (b) comprising a glycol solvent as a reducing agent under a basic condition, and step (b) is operated at the temperature higher than 120° C.

10 Claims, No Drawings

PROCESS FOR PREPARING A CATALYST FOR ALKANE AROMATIZATION

TECHNICAL FIELD

Chemistry relates to the field of a chemical composition and a process for preparing a catalyst for alkane aromatization.

BACKGROUND OF THE INVENTION

At present, aromatics such as benzene, toluene, ethylbenzene, o-xylene, m-xylene, and p-xylene are important intermediate petrochemical products because they are widely used in the preparation process of styrene, polyester fiber, nylon 6,6, phenol, and terephthalic acid.

It is well known that the aromatics can be generally prepared from reforming reaction of a heavy naphtha having 7 to 12 carbon atoms by dehydrocyclization reaction on $Pt/Cl$—$Al_2O_3$ catalyst. The said reaction has to use the heavy naphtha as a raw material, leading to a limitation of the utilization of cheaper light naphtha. Therefore, there have been continuously attempts to develop catalyst for the production of aromatics from light naphtha or alkane having less than 7 carbon atoms.

It had been reported that zeolite is the catalyst that can convert short chain alkane to aromatics. Therefore, there have been many studies to develop the catalyst to have good properties and suitable for industry. However, said catalyst still yield undesired properties such as its lifetime, low selectivity of aromatics and p-xylene, and coke formation during used, etc.

U.S. Pat. Nos. 4,861,933 and 4,304,686 disclose the preparation process of aromatics from an aliphatic hydrocarbon using gallium loaded zeolite catalyst. However, it was found that the selectivity of the mixture of benzene, toluene, and xylene (BTX) was low, so that it required further processes to separate and purify for industrial applications.

EP 0841092 discloses the formation reaction of hydrocarbon to give less coke formation and high yield of light olefin. The catalyst being used in said process was zeolite subjected to silylation reaction with silylating agent and treated with steam or acid. Nevertheless, it was found that said improved catalyst gave low aromatics yield.

US 20130237734 discloses the preparation process of aromatization catalyst comprising the step of contacting zeolite with organic acid, then contacting the obtained zeolite with group IB metal and group IIIA metal solutions, and then contacting with silylating agent. It was found that zeolite treated with organic acid especially oxalic acid provided higher aromatics yield.

US 20130172648 discloses the catalyst and the preparation process of the catalyst for the production of aromatics from propane. Said catalyst was prepared by treating zeolite with about 0.2 to 2% by weight of gallium and about 0.01 to 2% by weight of palladium or platinum metal. The said treatment was done by impregnation and ion exchange. However, this document did not disclose the efficiency of the said reaction on the selectivity of p-xylene.

From all above, this invention aims to prepare the catalyst for alkane aromatization in order to provide high % conversion, high selectivity of aromatics, and high selectivity of p-xylene in xylene.

SUMMARY OF INVENTION

The present invention relates to the process for preparing a catalyst for alkane aromatization, wherein said process comprises the following steps:

(a) contacting a zeolite with a solution of group IIIA metal salt;

(b) contacting the zeolite obtained from step (a) with the solution of metal salt selected from group VIIB metal, group VB metal, or a mixture thereof; and (c) contacting the zeolite obtained from step (b) with alkoxysilane, characterized in that the solution of metal salt in step (b) comprising a glycol solvent as a reducing agent under a basic condition, and step (b) is operated at the temperature higher than 120° C.

DESCRIPTION OF THE INVENTION

The present invention relates to the process for preparing a catalyst for alkane aromatization as described according to the following embodiments.

Any aspect showed herein refers including the its application to other aspects of this invention unless stated otherwise.

Technical terms or scientific terms used herein have definitions as understood by those having an ordinary person skilled in the art unless stated otherwise.

Any tools, equipment, methods, or chemicals mentioned herein mean tools, equipment, methods, or chemicals commonly operated or used by person skilled in the art unless explicated otherwise that they are tools, equipment, methods, or chemicals specific only in this invention.

Use of singular noun or singular pronoun with "comprising" in claims or specification refers to "one" and also "one or more", "at least one", and "one or more than one".

All compositions and/or methods disclosed and claimed in this application aim to cover embodiments from any action, performance, modification, or adjustment without any experiment that significantly different from this invention, and obtain with objected with utility and resulted as same as the present embodiment according to a person ordinary skilled in art although without specifically stated in claims. Therefore, substitutable or similar object to the present embodiment including any little modification or adjustment that clearly seen by a person skilled in art should be construed as remains in spirit, scope, and concept of invention as appeared in appended claims.

Throughout this application, term "about" means any number that appeared or showed herein that could be varied or deviated from any error of equipment, method, or personal using said equipment or method including variation or deviation caused from changes in physical properties.

Hereafter, invention embodiments are shown without any purpose to limit any scope of the invention.

This invention relates to the process for preparing a catalyst for alkane aromatization, wherein said process comprises of the following steps:

(a) contacting a zeolite with a solution of group IIIA metal salt;

(b) contacting the zeolite obtained from step (a) with the solution of metal salt selected from group VIIB metal, group VB metal, or a mixture thereof; and (c) contacting the zeolite obtained from step (b) with alkoxysilane, characterized in that the solution of metal salt in step (b) comprising a glycol solvent as a reducing agent under a basic condition, and step (b) is operated at the temperature higher than 120° C.

In one embodiment, the glycol solvent is alkylene glycol, preferably propylene glycol and ethylene glycol, most preferably ethylene glycol.

Preferably, step (b) is operated at the temperature in a range of 140 to 190° C. in order to reduce metal in step (b) to nano-size metal providing a good distribution in the zeolite.

Zeolite according to the invention comprises of aluminosilicate compound comprising silicon, aluminium, and oxygen in its structure. This can be natural or synthetic zeolite.

In one embodiment, the mole ratio of silica to alumina in the zeolite being used in the invention is more than 20, preferably in a range of about 20 to 80, and most preferably in the range of about 20 to 50.

In one aspect, zeolite may be selected from, but not limited to MFI zeolite selected from ZSM-5, ZSM-11, or a mixture thereof, most preferably ZSM-5.

In one embodiment, group IIIA metal is gallium. The group IIIA metal salt may be selected from gallium nitrate, gallium chloride, gallium bromide, gallium hydroxide, and gallium acetate, preferably gallium nitrate.

In one aspect, the ratio of group IIIA metal to zeolite in step (a) is in the range of about 0.5 to 2% by weight, preferably in the range of about 0.5 to 1% by weight.

In one aspect, step (a) is operated by an impregnation or an ion exchange, preferably ion exchange.

In one aspect, step (a) is operated at the temperature from room temperature to 100° C., preferably in the range of 50 to 90° C.

In one embodiment, group VIIIB metal may be selected from nickel, palladium, and platinum, preferably palladium.

In one aspect, the group VIIIB metal salt may be selected from nickel nitrate, nickel chloride, nickel bromide, platinum hydroxide, platinum nitrate, platinum chloride, platinum bromide, platinum hydroxide, palladium nitrate, palladium chloride, palladium bromide, palladium hydroxide, or a mixture thereof, preferably nickel nitrate, platinum chloride, and palladium chloride, most preferably palladium chloride.

In one embodiment, the group VB metal may be selected from vanadium and niobium, preferably niobium.

In one aspect, the group VB metal salt may be selected from vanadium nitrate, vanadium chloride, vanadium bromide, vanadium hydroxide, vanadium acetate, niobium nitrate, niobium chloride, niobium bromide, niobium hydroxide, niobium acetate, ammonium niobium oxalate, or a mixture thereof, preferably vanadium chloride and ammonium niobium oxalate, most preferably ammonium niobium oxalate.

In one embodiment, the ratio of group VIIIB metal and group VB metal to zeolite in step (b) is in a range of about 0.1 to 1% by weight, preferably in the range of about 0.1 to 0.5% by weight.

In one embodiment, step (c) may be done by a chemical vapor deposition method or a chemical liquid deposition method, preferably the chemical liquid deposition method.

For the chemical liquid deposition method, alkoxysilane in a solution form is used. The solvent for dissolving the alkoxysilane solution can be selected from, but not limited to aromatic hydrocarbon, aliphatic hydrocarbon, cyclic hydrocarbon, alicyclic hydrocarbon, cyclic olefin, and ether, preferably cycloalkane.

In one embodiment, alkoxysilane in step (c) may be selected from primary alkoxysilane, secondary alkoxysilane, tertiary alkoxysilane, quaternary alkoxysilane, or a mixture thereof, preferably quaternary alkoxysilane selected from tetramethoxysilane and tetraethoxysilane, most preferably tetraethoxysilane.

In one embodiment, the ratio of alkoxysilane to the zeolite in step (c) is in the range of about 5 to 20% by weight.

In one aspect, the concentration of a solution of alkoxysilane in step (c) is in a range of about 1 to 30% by volume.

In one embodiment, step (c) may be performed at the temperature in a range of about 20 to 50° C. for about 5 to 20 hours.

In one embodiment, the preparation process for said catalyst may further comprising the drying and calcination steps.

The drying step may be performed by a general drying method using oven, vacuum drying, and stirring evaporation.

The calcination step may be performed under an atmosphere for about 1 to 10 hours at the temperature in a range of about 400 to 800° C., preferably about 4 to 6 hours at the temperature in the range of about 500 to 600° C.

In another embodiment, the present invention relates to the use of catalyst prepared from the process according to the invention for the aromatization reaction of alkane having 4 to 9 carbon atoms in order to produce aromatics, preferably a mixture of benzene, toluene, and xylene (BTX), most preferably p-xylene.

In one embodiment, aromatization reaction may be performed by contacting alkane feed with catalyst prepared from the process according to the invention at the suitable conditions for the reaction. This can be operated by a fixed bed system, a moving bed system, a fluidized bed system, or a batch system.

The alkane aromatization reaction may be performed at the temperature in the range of about 400 to 800° C., preferably in a range of about 500 to 600° C., and at the pressure under an atmospheric pressure to about 3,000 kPa, preferably in the range of about 100 to 500 kPa, most preferably at atmospheric pressure.

Weight hourly space velocity (WHSV) of alkane feed in the alkane aromatization reaction is in a range of about 1 to 30 $hour^{-1}$, preferably in the range of about 3 to 10 $hour^{-1}$.

Generally, any person skilled in this field of art can be modify the alkane aromatization reaction conditions as suitable to types and compositions of catalyst feed and reactor systems.

The following examples are demonstrated as one aspect of the invention, not for limiting the scope of this invention in any way.

Preparation of Catalyst

The preparation of catalyst according to the invention may be prepared by the following methods.

Contacting with the Solution of Group IIIA Metal Salt

Zeolite was contacted with the solution of metal salt by ion exchange method using about 150 mL of a solution of gallium nitrate at the ratio of gallium to zeolite about 1% by weight. Then, the obtained mixture was stirred at the temperature about 80° C. for about 10 hours. The obtained mixture was washed with distilled water and dried under the temperature about 110° C. overnight. Then, it was calcinated under the air temperature about 550° C. for about 5 hours. The calcination temperature was raised up from room temperature at the rate about 10° C. per minute.

Contacting with the Solution of Group VB or Group VIIIB Metal Salt or Group Containing Glycol Solvent The metal chloride salt was added to about 50 mL of ethylene glycol. The metal to zeolite ratio was about 0.5% by weight. The pH of solution was adjusted to about 10. Then, the zeolite was added about 2 g and refluxed at the temperature about 180° C. for about 3 hours. Then, the obtained mixture was filtered and washed with acetone and distilled water and dried at the temperature about 110° C. overnight. Then, it was calcinated under the air temperature about 550° C. for about 5 hours. The calcination temperature was raised up from room temperature at the rate about 10° C. per minute.

Contacting with Alkoxysilane

About 1 g of the zeolite was contacted with the solution of tetraethoxysilane with the ratio of tetraethoxysilane to the zeolite about 25% by weight for about 12 hours. Then, it was dried at the temperature about 120° C. for about 2 hours. Then, it was calcinated under the air at temperature about 550° C. for about 5 hours. The calcination temperature was raised up from room temperature at the rate about 10° C. per minute.

Comparative Sample Cat A (Ga/ZSM5)

Zeolite with the mole ratio of silica to alumina about 25 was contacted with the solution of gallium nitrate by the method described above.

Comparative Sample Cat B (Pd(imp)/Ga/ZSM5)

Zeolite with the mole ratio of silica to alumina about 25 was contacted with the solution of gallium nitrate by the method described above. The obtained zeolite was contacted with palladium chloride with the ratio of palladium to zeolite about 0.5% by weight. The obtained zeolite was dried at the temperature about 110° C. overnight, and calcinated under the air temperature about 550° C. for about 5 hours, wherein the calcination temperature was raised up from room temperature at the rate about 10° C. per minute.

Comparative Sample Cat C (Pd(glycol)/Ga/ZSM5)

Zeolite with the mole ratio of silica to alumina about 25 was contacted with the solution of gallium nitrate. Then, the obtained zeolite was contacted with the solution of palladium chloride containing glycol solvent by the method described above.

Comparative Sample Cat D (CLD/Pd(imp)/Ga/ZSM5)

The comparative sample Cat D was prepared by the method described in the comparative sample Cat B. Then, the obtained zeolite was contacted with tetraethoxysilane according to the method described above.

Sample According to the Invention Cat 1 (CLD/Pd(glycol)/Ga/ZSM5)

The sample according to the invention Cat 1 was prepared by the method described in comparative sample Cat C. Then, the obtained zeolite was contacted with tetraethoxysilane according to the method described above.

Sample According to the Invention Cat 2 (CLD/Nb(glycol)/Ga/ZSM5)

The sample according to the invention Cat 2 was prepared by the method described in sample according to the invention Cat 1 using a solution of niobium chloride instead of the solution of palladium chloride.

Sample According to the Invention Cat 3 (CLD/V(glycol)/Ga/ZSM5)

The sample according to the invention Cat 3 was prepared by the method described in sample according to the invention Cat 1 using a solution of vanadium chloride instead of a solution of palladium chloride.

Testing of Alkane Aromatization Reaction

The testing of alkane aromatization reaction may be performed by the following conditions:

The alkane aromatization reaction was operated in fixed-bed reactor. About 0.2 g of the catalyst was used prior to the reaction. The catalyst was contacted with hydrogen at the temperature about 500° C. for about 1 hours. Then, hydrogen was transformed to nitrogen with a flow rate about 20 mL/min. Then, pentane was fed with the flow rate about 1.6 mL/hour. The reaction was operated at the temperature about 500° C. at atmospheric pressure and the weight hourly space velocity (WHSV) was about 5 hour$^{-1}$.

The followings are testing examples of compositions of the products obtained from the catalyst according to the invention. Methods and equipment used for each testing are methods and equipment being used generally and not intended to limit the scope of the invention.

Compositions of products were determined by a gas chromatography technique (Shimadzu 17A-GC, HP-PLOT/Al2O3 "S" deactivated capillary column). The temperature of column was set to separate each composition in the products. The starting temperature was kept at 40° C. for about 10 minutes. Then, the temperature was raised at a linear rate to the temperature about 195° C. and being kept stable for about 30 minutes. The compositions of xylene isomers were analyzed using Agilent Model 6890N equipped with Stabilwax capillary column.

The % conversion, % yield, % selectivity of the product in each composition and % selectivity of p-xylene in xylene were calculated from the following equations:

$$\% \text{ conversion} = \frac{\text{amount of reacted reactant}}{\text{amount of reactant in feed}} \times 100$$

$$\% \text{ selectivity of aromatics} = \frac{\text{amount of (benzene + toluene + xylene)}}{\text{amount of total product}} \times 100$$

$$\% \text{ selectivity of } p\text{-xylene} = \frac{\text{amount of } p\text{-xylene}}{\text{amount of } (p\text{-xylene} + m\text{-xylene} + o\text{-xylene}} \times 100$$

TABLE 1

% conversion, % selectivity of aromatics, and % selectivity of p-xylene at time on stream of 4 hours

| Sample | % conversion | % selectivity of aromatics | % selectivity of p-xylene |
|---|---|---|---|
| Comparative sample Cat A | 78.92 | 37.91 | 23.13 |
| Comparative sample Cat B | 58.31 | 43.69 | 28.54 |
| Comparative sample Cat C | 65.85 | 48.98 | 28.91 |
| Comparative sample Cat D | 44.61 | 48.42 | 45.50 |
| Sample according to the invention 1 | 58.54 | 54.78 | 44.54 |
| Sample according to the invention 2 | 69.73 | 50.18 | 47.79 |
| Sample according to the invention 3 | 64.82 | 50.53 | 47.56 |

Table 1 shows the efficiency of comparative samples and samples according to the invention for alkane aromatization reaction. From the table, the comparing comparative sample Cat B, comparative sample Cat C and comparative sample Cat D to sample according to the invention 1, it was found that comparative sample Cat C treated with the solution of palladium chloride containing the glycol solvent as the reducing agent gave higher % conversion and % selectivity of aromatics.

Moreover, it was found that the catalyst prepared from the process according to the invention gave high % conversion, high % selectivity of aromatics, and high % selectivity of p-xylene for the alkane aromatization reaction as being stated in the objectives of this invention.

Best Mode or of the Invention

Best mode of the invention is as provided in the description of the invention.

The invention claimed is:

1. A process for preparing a catalyst for alkane aromatization, wherein said process comprises the following steps:
   (a) contacting a zeolite with a solution of group IIIA metal salt, wherein the group IIIA metal in step (a) is gallium; then
   (b) contacting the zeolite obtained from step (a) with the solution of a group VIM metal salt; and then
   (c) contacting the zeolite obtained from step (b) with alkoxysilane,
   characterized in that the solution of metal salt in step (b) comprising a glycol solvent as a reducing agent under a basic condition, and step (b) is operated at the temperature higher than 120° C.

2. The process for preparing a catalyst according to claim 1, wherein the glycol solvent is alkelyne glycol.

3. The process for preparing a catalyst according to claim 1, wherein the glycol solvent is ethylene glycol.

4. The process for preparing a catalyst according to claim 2, wherein the glycol solvent is ethylene glycol.

5. The process for preparing a catalyst according to claim 1, wherein step (b) is operated at the temperature in a range of 140 to 190° C.

6. The process for preparing a catalyst according to claim 1, wherein the zeolite is selected from ZSM-5, ZSM-11, or a mixture thereof.

7. The process for preparing a catalyst according to claim 1, wherein the ratio of group IIIA metal to zeolite in step (a) is in the range of 0.5 to 2% by weight.

8. The process for preparing a catalyst according to claim 1, wherein the ratio of group IIIA metal to zeolite in step (a) is in the range of 0.5 to 2% by weight.

9. The process for preparing a catalyst according to claim 1, wherein group VIIIB metal is palladium and group VB metal is vanadium or niobium.

10. The process for preparing a catalyst according to claim 1, wherein the ratio of alkoxysilane to zeolite in step (c) is in the range of 5 to 20% by weight.

* * * * *